(12) United States Patent
Torrent Campmany

(10) Patent No.: US 8,377,485 B2
(45) Date of Patent: Feb. 19, 2013

(54) ANTIMICROBIAL COMPOSITION AND USE THEREOF

(75) Inventor: Joan Torrent Campmany, Paraiso (BR)

(73) Assignee: Oligo Basics Industria e Comercio de Racao Ltda, Parana (BR)

( * ) Notice: Subject to any disclaimer, the term of this patent is extended or adjusted under 35 U.S.C. 154(b) by 0 days.

(21) Appl. No.: 11/844,011

(22) Filed: Aug. 23, 2007

(65) Prior Publication Data

US 2008/0226760 A1    Sep. 18, 2008

(30) Foreign Application Priority Data

Mar. 16, 2007   (BR) ..................................... 0700927

(51) Int. Cl.
*A01N 65/00* (2009.01)
(52) U.S. Cl. ..................................................... 424/725
(58) Field of Classification Search ........................ None
See application file for complete search history.

(56) References Cited

U.S. PATENT DOCUMENTS

| | | | |
|---|---|---|---|
| 4,670,469 A * | 6/1987 | Schewe et al. | 514/575 |
| 5,725,894 A | 3/1998 | Toyomizu et al. | |
| 5,776,919 A | 7/1998 | Sukigara et al. | |
| 6,379,694 B1 * | 4/2002 | Hatano et al. | 424/442 |
| 2006/0140881 A1 * | 6/2006 | Xu et al. | 424/49 |
| 2006/0204453 A1 * | 9/2006 | Giniger | 424/49 |

FOREIGN PATENT DOCUMENTS

JP          403240721    * 10/1991

OTHER PUBLICATIONS

Novak et al., "Antimicrobial Ativity of Some Ricinoleic and Oleic Acid Derivatives" J. Amer. Oil Chemi. Soc. 38:321-324.
Eichbaum, "Biological Properties of Anacardic Acid (O-Penta-Decadienyl-Salicylic Acid and Related Compounds" 1946. Mem. Inst. Butantan, 19:71-96.
Gellerman et al. "Antimicrobial effects of anacardic acids" 1969. Can J. Microbiol. 15: 1219-1223.

* cited by examiner

*Primary Examiner* — Michael Meller
(74) *Attorney, Agent, or Firm* — Baker, Donelson, Bearman, Caldwell & Berkowitz, PC

(57) ABSTRACT

This invention relates to compositions with broad antimicrobial activity against bacteria, fungi, and protozoans. The compositions and methods of the present invention can be used in the prevention and treatment of pathogenic processes in people and animals by any administration method (oral, topical, or parenteral), as a performance improver in animals, infection controller in fermentations, and preserver of grains, seeds, and food for animals and/or people.

1 Claim, No Drawings

ANTIMICROBIAL COMPOSITION AND USE THEREOF

This application claims priority to Brazilian Patent Application No. PI 0700927, filed Mar. 16, 2007, the entire contents of which is incorporated by reference in its entirety.

FIELD OF APPLICATION

This invention relates to a composition and methods with broad antimicrobial activity against bacteria, fungi, and protozoans. The composition and methods can be used in the prevention and treatment of pathogenic processes in people and animals by any administration method (oral, topical, or parenteral), as a performance improver in animals, infection controller in fermentations, and preserver of grains, seeds, and food for animals and/or people.

FIELD OF THE INVENTION

This invention is related to an antimicrobial composition effective against bacteria, fungi, and protozoans, and can be used in superior animals in the control of fermentations and as an antifungic for food and seeds.

STATE OF THE ART

New regulatory measures, as well as the appearance of resistance to several antibiotics, have increased the search for alternative solutions, particularly those using natural products.

Some areas, such as the animal production, have faced the appearance of prevalent problems like coccidiosis, particularly in poultry and piglets. Antibiotics are used to prevent the appearance of this disease. The antibiotics most commonly used in aviculture are ionophores like monensin, salinomycin, or lasalocid. These products must be used continuously in feed to prevent the disease, and due to the continued use, resistance appears very frequently. This fact forces producers to apply double programs, where the elected drug is changed in the middle of the weight gain process. These double programs usually change twice a year in order to prevent such resistance to antibiotics. Vaccines are also used to prevent the disease, but the secondary effects caused by vaccination end up raising the animal production cost.

Performance improver products for animals most commonly used are also antibiotics used in subtherapeutic doses. Concerns deriving from the appearance of resistance to these antibiotics, particularly when such resistance is accomplished by bacteria that might affect the human health, have forced regulatory authorities all over the world to ban the use of many antibiotics as animal performance improvers. Similarly, concerns with the possible antibiotic residues in animal products for human consumption have resulted in longer removal periods for these drugs. Longer removal periods result in longer periods in which animals are unprotected against a large number of diseases, and therefore have resulted in an increased use of drugs in a therapeutic level, as well as increased production costs.

Industrial fermentation process using yeast, for instance, the production of ethanol, may experience infections in the fermentation process, where bacteria grow at the same time as the yeast, competing for nutrients, with the possibility to inhibit the growth of the yeast. These infections are treated with antibiotics of the same type as those used in the animal or human health. Additionally to the obvious risks of resistance development, yeast is dried and used in human food or animal feed. The use of an antibiotic during fermentation makes the use of that yeast unfeasible both for the human food and animal feed, since the possible antibiotic residues could pose risks to the health of people and animals.

The storage of food for a long period is a delicate process because the growth of fungi occurs when the food is not stored properly. The products more commonly used to preserve food and grains against fungi are those derived from the propionic acid, since they are relatively cheap and do not pose risks to the human health. However, the propionic acid cannot be used in seeds, as it kills the seed and causes it not to sprout. For this reason, products that do not affect the germination of the seed, but having a high toxicity against human beings and animals are employed. On the other hand, the propionic acid is a volatile product that, when used in high doses, may change the taste of food and, therefore, cannot prevent the growth of fungi in long periods in the doses used to protect food.

The resistance to antibiotics has become a public health matter and has increased the cost of animal production and treatment. Therefore, the development of a natural product with antimicrobial activity that does not pose resistance and toxicity problems is a great accomplishment in the animal production industry, both for the animal and human health. The ricinoleic acid is a natural product considered as a food fat. It has no toxicity and had previously only been used in topical formulations for its laxative effects in oral administration.

Document U.S. Pat. No. 5,725,894 presents an anticoccidial agent comprising the cashew nut oil and/or anacardic acid.

Document U.S. Pat. No. 5,776,919 presents an antibacterial composition active against *Staphylococcus aureus* resistant to methicillin, comprising methicillin and a promoter of antibacterial activity in the family of 2-hydroxy-6-R-benzoic acid.

Document U.S. Pat. No. 6,379,694 presents a composition or food supplement to treat or prevent coccidiosis, containing cashew nut oil and/or anacardic acid, and at least one substance selected from organic compounds of zinc, betaines, and microorganisms in gender *Bacillus*.

Thus, in the present invention an antimicrobial composition has been developed according to the following objectives:
- to present great safety for the health of animals or human beings to which the composition is administered, not posing side effects;
- not to cause deterioration of its effects due to the resistance to other drugs;
- to offer great healing effects against infections by fungi, bacteria, or protozoans;
- to provide a composition that could be produced at a reasonable cost;
- not to leave residues in the meat, milk, or eggs of treated animals.

SUMMARY OF THE INVENTION

This invention relates to an antimicrobial composition that can be applied to people and animals without secondary effects by any application method to prevent and treat diseases caused by bacteria, fungi, and protozoans. It can be used in grains, seeds, and food for animals and humans, and also to control infections in fermentations. This composition does not leave toxic residues in food or in the carcass of animals. No adverse or secondary effects are known. It can be used throughout the entire life of animals, as no microbial resistance is known.

This invention relates to a composition comprising a hydroxylated fatty acid (such as the ricinoleic acid) or a triglyceride containing hydroxylated fatty acid in its composition (such as the castor oil) combined with the liquid from the cashew nut peel and/or any of its agents (cardol, cardanol, and anacardic acid) and/or organic acids.

DETAILED DESCRIPTION OF THE INVENTION

An antimicrobial composition was developed with the following weight in proportion to the total mass of the mixture:
(a) about 2 to about 100% in weight compared to the total mass of the composition of one or more hydroxylated fatty acids with 10 to 20 atoms of carbon in its chain, or one or more triglycerides containing one or more hydroxylated fatty acids with 10 to 20 atoms of carbon in its chain;
(b) 0 to about 95% in weight compared to the total mass of the composition of one or more compounds from the cashew or from species in the Anacardiaceae family, or also any of the following compounds: cardol, cardanol, or anacardic acid from such species or obtained by synthesis;
(c) 0 to about 95% in weight compared to the total mass of the composition of one or more organic acids having 2 to 20 atoms of carbon in its chain.

The compositions in this invention can be useful in the following situations:
treatment and prevention of bacterial, fungal, and protozoal infections in people and animals, administered in oral, topical, or parenteral methods;
as anticoccidial and performance improvers in animals;
in the control of bacterial infections during the fermentation made with yeast;
in the control of the fungal growth in grains, seeds, and food for animals and people.

The hydroxylated fatty acid containing 10 to 20 atoms of carbon in its chain, used in this invention, can be used as ricinoleic acid or hydroxystearic acid, or triglyceride, containing ricinoleic or hydroxystearic acid in its composition, such as the castor oil. The ricinoleic acid has antibiotic effect against gram-positive bacteria and fungi (Novak et al., 1961, J. Amer. Oil Chem. Soc. 38:321-324). However, its use as an oral antibiotic and as an antiprotozoal agent has not been previously reported in the scientific literature.

As for organic acids, the short chain fatty acids, such as the formic, lactic, acetic, propionic, butyric, malic, or citric acids are known for their antibacterial activity, particularly at low pHs, both for gram-positive and gram-negative bacteria. Organic acids known as medium chain (C6 to C12), caprylic, capric, caproic, and lauric acids have known activity against gram-positive bacteria, fungi, and protozoans. At the same time, capric and caprylic acids also have action against gram-negative bacteria.

The cashew nut liquid has components with antibiotical action, particularly against gram-positive bacteria, fungi, and protozoans (Eichbaum, 1946. Mem. Inst. Butantan, 19:71-96; Gellerman et al., 1969. Can. J. Microbiol. 15:1219-1223). The liquid extracted from the cashew nut may be in its raw state or have undergone thermal treatment due to the fact that it was obtained as a byproduct of fried cashew nuts.

This invention enables a composition with a strong antimicrobial action due to its activity against gram-positive, gram-negative bacteria, fungi, and protozoans.

Another advantage is its extremely low toxicity, when compared to other antibiotics. While traditional antibiotics show toxicity at relatively low doses, these compositions are nontoxic and could only be laxative by oral means at extremely high doses.

The ricinoleic acid is a natural product considered as a food fat. It has no toxicity and had previously only been used in topical formulations for its laxative effects in oral administration. However, when used in low doses, alone, or associated to other natural products, such as cashew nut liquid (*Anacardium occidentale*) or organic acids, the ricinoleic acid can be ingested without secondary laxative effects orally. The mixture of ricinoleic acid with the cashew nut liquid and/or organic acids presents a synergic action, improving its action and also expanding the type of microorganisms against which the composition has effect.

When the ricinoleic acid is used jointly with the cashew nut liquid, the doses in the two products decrease, allowing for lower doses and increasing the safety in the composition.

The organic acids allow the composition to have better effect against gram-negative bacteria.

The composition of the components of the invention will vary depending on the administration method and the purpose of the use. However, the percentages of ricinoleic acid may vary from 2 to 100%; the percentages of cashew nut liquid, from 0 to 95%; and the percentages of organic acids, from 0 to 95% in weight, compared to the total mass of the mixture. Castor oil, cashew nut liquid, and optionally formic acid are preferably used.

These compositions may be applied directly or through solid and liquid carriers, to facilitate the application of the product, depending on the application method. When used through oral methods, they can also be applied directly into the mouth of humans or animals, with or without a carrier, or mixed with food.

Appropriate carriers are those that do not interfere with the release of active components.

The administration of compositions will vary in accordance to the user's objective. When the intention is to have a performance improver or anticoccidial effect in animals, the composition must be applied to the animal feed throughout the entire life of the animal, or during the period in which a microbial challenge is expected. When the compositions are used to treat enteric problems previously existing in companion animals or piglets, one or two applications within 24 hours are usually sufficient to solve the problem.

In the case of topical applications, the ideal is to apply the composition daily on the affected area until a complete healing of the condition.

The dosing of the invention depends on the objective. However, when the composition is used in animals as a prevention, performance improver, anticoccidial, during continued treatments, in the control of fermentation, and as a preserver of food and seeds, the dose must be between about 10 and about 5000 ppm, in proportion to the total mass of the food, feed, grains, seeds, or the culture means in fermentations, or mass of yeast to be treated. When it is used for a rapid treatment directly into the mouth of the animal or through oral means in humans, it can vary from 0.1 to 3 grams/kg of living weight. When used topically or parenterally, the amount of carrier can vary from 0 to 90% compared to the mass of the composition.

Below are some examples of forms to prepare the invention. However, these examples should not be taken as limiting effects to the scope of the invention. The compositions with different percentages of ricinoleic acid, cashew nut liquid and/or organic acids will be referred to as AC (antimicrobial composition).

Example 1

One hundred and twenty chicks at one day of age were randomly distributed into four treatments with three repetitions of ten animals. The treatments were: non-inoculated control, inoculated control, AC at 500 ppm, and AC at 1000 ppm. The AC composition was 50% castor oil: 50% formic acid. The birds were fed with commercially available feeds that met or exceeded the nutritional requirements of the National Research Council (NRC). At the ninth day of age, the birds were inoculated with 20.000 oocysts/bird of *Eimeria maxima*, with 0.5 mL of inocula. Seven days after the inoculation, the birds were sacrificed in order to evaluate the degree of intestinal lesion.

TABLE 1

Results of the degree of intestinal lesion (0 - no lesion, 4 - maximum lesion).

| Treatment | Degree of intestinal lesion |
|---|---|
| Non-inoculated treatment | 0.0 |
| Inoculated treatment | 1.18 |
| AC at 500 ppm | 0.93 |
| AC at 1,000 ppm | 0.78 |

Example 2

Seven hundred and twenty chickens were randomly distributed into four treatments with six repetitions each, with 30 animals in each repetition. The birds were placed in a conventional yard divided into boxes.

The four treatments were (1. Non-inoculated, without anticoccidial; 2. Inoculated without anticoccidial; 3. Inoculated-salinomycin (66 ppm); 4. inoculated-AC (1500 ppm)). The birds were inoculated at the 18$^{th}$ day of age with 0.5 liter of inocula containing 10,000, 9,000, and 8,000 sporulated oocysts of *Eimeria tenella, Eimeria maxima*, and *Eimeria acervulina*, respectively. This solution was mixed with the feed and offered to each group of 30 birds. At the 24$^{th}$ day of age, the degree of intestinal lesion was evaluated (0—no lesion, 4—maximum lesion). The AC composition was 12% castor oil, 40% cashew nut liquid, and 48% carrier.

The experimental design utilized seven hundred and twenty chickens which were randomly distributed into four treatments and six repetitions. The averages were compared using the SNK test (Student-Newman-Keuls).

TABLE 2

Performance results from the first to the 40$^{th}$ day of age.

| Treatment | Initial weight, g | Final weight, g | Weight gain, g | Ingestion, g | Alimentary conversion | Viability |
|---|---|---|---|---|---|---|
| Non-inoculated without anticoccidial | 44.9 a | 2443 a | 2398 a | 4185 a | 1.75 a | 98.1 a |
| Inoculated without anticoccidial | 44.1 a | 2288 b | 2244 b | 4136 ab | 1.85 a | 95.7 a |
| Inoculated-salinomycin | 43.7 a | 2305 b | 2261 b | 4018 bc | 1.78 a | 97.5 a |
| Inoculated-AC | 45.0 a | 2254 b | 2209 b | 4015 bc | 1.82 a | 97.0 a |
| CV | 3.37 | 4.54 | 4.61 | 2.50 | 3.54 | 3.52 | a b Averages in the same column with different letters differ (P < 0.05) in the SNK test (Student-Newman-Keuls).

TABLE 3

Results of the degree of intestinal lesion

| Treatment | E. acervulina | E. maxima | E. tenella |
|---|---|---|---|
| Non-inoculated w/o anticoccidial | 0.00 | 0.00 | 0.00 |

TABLE 3-continued

Results of the degree of intestinal lesion

| Treatment | E. acervulina | E. maxima | E. tenella |
|---|---|---|---|
| Inoculated w/o anticoccidial | 1.11 a | 1.17 a | 1.78 a |
| Inoculated-salinomycin | 0.72 b | 0.72 a | 1.61 a |
| Inoculated-AC | 0.67 b | 1.20 a | 1.13 b | ab Averages in the same column with different letters differ (P < 0.05).

Example 3

One thousand and two hundred chicks on the 1st day of age were distributed into six treatments with four repetitions and 50 birds per repetition. The treatments are shown in table 4. The animals were slaughtered on the 40th day of age, and weight gain and food conversion was calculated. The AC composition was 12% castor oil, 40% cashew nut liquid, and 48% carrier.

TABLE 4

Results of the use of AC with or without performance improvers.

| Treatment | Average weight Kg | Conversion | Conversion adjusted at 2.8 kg |
|---|---|---|---|
| Negative control | 3.026 | 1.658 | 1.601 |
| Salinomycin + Zinc Bacitracin + Halquinol | 3.026 | 1.665 | 1.603 |
| 1500 ppm AC | 3.012 | 1.627 | 1.583 |
| 1500 ppm + Zinc Bacitracin + Halquinol | 2.988 | 1.627 | 1.570 |
| 1000 ppm AC | 2.987 | 1.655 | 1.597 |
| 1000 ppm AC + Zinc Bacitracin + Halquinol | 2.969 | 1.648 | 1.598 |

Example 4

Ten goats were divided into a treated and controlled group. The treated group was supplemented with 0.8 g/animal/day of AC (12% castor oil, 40% cashew nut liquid, and 48% carrier). The animals were weighted and separated. The weights were recorded on 11th and 20th days from the inception of the trial. At the end of the trial, the animals supplemented with AC had a weight gain of 8% compared to the controlled group.

TABLE 5

Weight gains of animals with and without supplementation with AC.

| | Weight gain, g/d |
|---|---|
| CONTROL | 272 |
| AC | 297 |

Example 5

Seventy-five (75) castrated male piglets and seventy-five (75) female piglets (a total 150 animals) were distributed on the 21st day of age in 5 treatments with six repetitions, that is:
A—Control
B—AC at 500 ppm;
C—AC at 1000 ppm;
D—AC at 1500 ppm;
E—AC at 2000 ppm.
The AC composition was: 12% castor oil, 40% cashew nut liquid, and 48% carrier.

TABLE 6

Performance of male piglets on 21st to 35th day of age supplemented with different AC levels.

| | Inclusion level (ppm) | | | | | |
|---|---|---|---|---|---|---|
| | 0 | 500 | 1000 | 1500 | 2000 | CV(%) |
| Initial weight (21 days, kg) | 6.50 | 6.50 | 6.49 | 6.48 | 6.49 | — |
| Final weight (35 days, kg) | 8.47 | 8.31 | 8.62 | 8.60 | 8.80 | 3.81 |
| Intake | 22.75 | 218.50 | 221.25 | 218.00 | 244.50 | 12.14 |
| Average daily gain, g | 140.84 | 129.55 | 152.16 | 151.69 | 164.38 | 13.07 |
| Food conversion (g/g) | 1.70 a | 1.84 c | 1.51 b | 1.54 b | 1.56 b | 8.82 | ab Averages with different levels differ (P < 0.05) by Dunnett test.

Example 6

Piglets (n=102) from nine swinish matrices infected by *Isospora suis* were divided into two treatments. Sixty-five piglets of those females were supplemented with 1 ml of AC (composition: 6% castor oil, 24% cashew nut liquid, and 70% carrier) on the 3rd day of age. The 37 remaining piglets were not supplemented. There was one case of diarrhea for the animals supplemented with AC compared to 13 animals of the control group.

TABLE 7

Effects of AC on a small farm infected by *Isospora suis*.

| Treatment | No. of matrices | No. of piglets | Cases of diarrhea |
|---|---|---|---|
| Control | 4 | 37 | 13 |
| AC | 5 | 65 | 1 |

Example 7

The purpose was to determine the antimicrobial action of a combination of cashew nut liquid and ricinoleic acid, and the effects on yeast (*Saccharomyces cerevisiae*) during alcoholic fermentation, response to different dosages and under acidic conditions.
The items below were evaluated:
  Laboratory fermentation with *Saccharomyces cerevisiae* by evaluating the feasibility and growth of yeast, in addition to bacteria developed at different concentrations of the products and mixtures;
  Evaluation of the deflocculation power of yeast in fermentations at several dosages of the products and mixtures;
  Evaluation of different dosages in the test for Sensitivity of Bacteria to define the quantity of products and mixtures to be recommended in the fermentation process by comparing them to other antibiotics previously tested and approved being used in the current market;
  Identification of the characteristics of products and mixtures during the handling;
  Evaluation of products and mixtures at low pH by simulating the conventional treatment of the yeast milk.
The studies were based on the cause vs. effect methodology, using the observation of the growth of microorganisms as a parameter for responses.
The tested products (P1-P5) are:
P1—100% Cashew nut liquid
P2—100% Ricinoleic Acid
P3—75% Cashew nut liquid+25% Ricinoleic Acid
P4—50% Cashew nut liquid+50% Ricinoleic Acid
P5—25% Cashew nut liquid+75% Ricinoleic Acid
Basically, five bacteria tests were carried out in which several dosages were tested of the products 1 to 5 under different conditions and by comparing them to other antibiotics previously known in the market.

TABLE 8

DETERMINATION OF SENSITIVITY OF BACTERIA

| | MAX | HJ | MAX | HJ | P1 | P1 | P1 | P1 | P1 | P1 | P1 | P1 |
|---|---|---|---|---|---|---|---|---|---|---|---|---|
| RESULTS P1 | 5 | 5 | 3 | 3 | 100 | 90 | 80 | 70 | 60 | 50 | 40 | 30 | T |

| | MAX | HJ | MAX | HJ | P2 | P2 | P2 | P2 | P2 | P2 | P2 | P2 |
|---|---|---|---|---|---|---|---|---|---|---|---|---|
| RESULTS P2 | 5 | 5 | 3 | 3 | 100 | 90 | 80 | 70 | 60 | 50 | 40 | 30 | T |

| | MAX | HJ | MAX | HJ | P3 | P3 | P3 | P3 | P3 | P3 | P3 | P3 |
|---|---|---|---|---|---|---|---|---|---|---|---|---|
| RESULTS P3 | 5 | 5 | 3 | 3 | 100 | 90 | 80 | 70 | 60 | 50 | 40 | 30 | T |

| | MAX | HJ | MAX | HJ | P4 | P4 | P4 | P4 | P4 | P4 | P4 | P4 |
|---|---|---|---|---|---|---|---|---|---|---|---|---|

TABLE 8-continued

DETERMINATION OF SENSITIVITY OF BACTERIA

| RESULTS P4 | 5 | 5 | 3 | 3 | 100 | 90 | 80 | 70 | 60 | 50 | 40 | 30 | T |
|---|---|---|---|---|---|---|---|---|---|---|---|---|---|
| | MAX | HJ | MAX | HJ | P5 | P5 | P5 | P5 | P5 | P5 | P5 | P5 | |
| RESULTS P5 | 5 | 5 | 3 | 3 | 100 | 90 | 80 | 70 | 60 | 50 | 40 | 30 | T |

Legend:
HJ = Kamoran HJ
MAX = MAX
T = Testimony

The performance of the products P1-P5 are presented in Table 8. The results for P1, P2, P3 and P4 show similar performance as indicated by the data shown from left to right beginning with the column headed "Max" (column 1) through column 9. Additionally, the performance results are decreasing in efficacy from left to right. For P1, P2, P3, and P4 negative results were obtained for the last three columns (columns 10-12, excluding column T). The results for P5 show similar performance as indicated by the data shown from left to right beginning with column 1 through column 10. Additionally, the performance results are decreasing in efficacy from left to right. For P5 negative results were obtained for the last two columns (columns 11-12, excluding column T).

The following numbers identifying the products are ppm, which have been dosed.

TABLE 9

DETERMINATION OF SENSITIVITY OF BACTERIA

| | FB | HJ | HJ | P1 | FB | P1 | P1 | P1 | PR | P1 | PR | P1 | P1 | P1 |
|---|---|---|---|---|---|---|---|---|---|---|---|---|---|---|
| RESULTS P1 | 5 | 5 | 3 | 100 | 3 | 90 | 80 | 70 | 5 | 60 | 3 | 50 | 40 | 30 | T |
| | P2 | FB | HJ | HJ | P2 | P2 | P2 | P2 | P2 | P2 | FB | P2 | PR | PR |
| RESULTS P2 | 100 | 5 | 5 | 3 | 90 | 80 | 70 | 60 | 50 | 40 | 3 | 30 | 5 | 3 | T |
| | FB | HJ | HJ | FB | P3 | P3 | P3 | P3 | P3 | P3 | P3 | P3 | PR | PR |
| RESULTS P3 | 5 | 5 | 3 | 3 | 100 | 90 | 80 | 70 | 60 | 50 | 40 | 30 | 5 | 3 | T |
| | FB | HJ | HJ | P4 | P4 | P4 | P4 | P4 | FB | P4 | P4 | P4 | PR | PR |
| RESULTS P4 | 5 | 5 | 3 | 100 | 90 | 80 | 70 | 60 | 3 | 50 | 40 | 30 | 5 | 3 | T |
| | FB | HJ | HJ | P5 | P5 | P5 | P5 | P5 | FB | P5 | P5 | P5 | PR | PR |
| RESULTS P5 | 5 | 5 | 3 | 100 | 90 | 80 | 70 | 60 | 3 | 50 | 40 | 30 | 5 | 3 | T |

Legend:
HJ = Kamoran HJ
PR = Prevent
FB = Free Bacter
T = Testimony

The performance of the products P1-P5 are presented in Table 9. The results for P1 show similar performance as indicated by the data shown from left to right beginning with the column headed "Max" (column 1) through column 5. Additionally, the performance results are decreasing in efficacy from left to right. For P1 negative results were obtained for columns 6-14 (excluding column T). The results for P2 show similar performance as indicated by the data shown from left to right beginning with column 1 through column 10. Additionally, the performance results are decreasing in efficacy from left to right. For P2 negative results were obtained for columns 11-14 (excluding column T). The results for P3 show similar performance as indicated by the data shown from left to right beginning with column 1 through column 3. For P3 negative results were obtained for columns 4-14 (excluding column T). The results for P4 and P5 show similar performance as indicated by the data shown from left to right beginning with column 1 through column 9. Additionally, the performance results are decreasing in efficacy from left to right. For P4 and P5 negative results were obtained for the last five columns (columns 10-14, excluding column T).

The following numbers identifying the products are ppm, which have been dosed.

TABLE 10

DETERMINATION OF SENSITIVITY OF BACTERIA

| | MAX | HJ | MAX | HJ | P1 | P1 | P1 | P1 | | | | |
|---|---|---|---|---|---|---|---|---|---|---|---|---|
| RESULTS P1 | 5 | 5 | 3 | 3 | 70 | 80 | 90 | 100 | | | | T |

| | MAX | HJ | MAX | HJ | P2 | P2 | P2 | P2 | P2 | P2 | P2 | |
|---|---|---|---|---|---|---|---|---|---|---|---|---|
| RESULTS P2 | 5 | 5 | 3 | 3 | 40 | 50 | 60 | 70 | 80 | 90 | 100 | T |

| | MAX | HJ | MAX | HJ | P3 | P3 | P3 | P3 | P3 | | | |
|---|---|---|---|---|---|---|---|---|---|---|---|---|
| RESULTS P3 | 5 | 5 | 3 | 3 | 60 | 70 | 80 | 90 | 100 | | | T |

| | MAX | HJ | MAX | HJ | P4 | P4 | P4 | P4 | P4 | P4 | P4 | |
|---|---|---|---|---|---|---|---|---|---|---|---|---|
| RESULTS P4 | 5 | 5 | 3 | 3 | 40 | 50 | 60 | 70 | 80 | 90 | 100 | T |

| | MAX | HJ | MAX | HJ | P5 | P5 | P5 | P5 | P5 | P5 | P5 | |
|---|---|---|---|---|---|---|---|---|---|---|---|---|
| RESULTS P5 | 5 | 5 | 3 | 3 | 40 | 50 | 60 | 70 | 80 | 90 | 100 | T |

Legend:
HJ = Kamoran HJ
MAX = MAX
T = Testimony

The results for P1 show similar performance as indicated by the data shown from left to right beginning with the column headed "Max" (column 1) through column 8 (excluding column T). The results for P2 show similar performance as indicated by the data shown from left to right beginning with column 1 through column 11 (excluding column T). The results for P3 show similar performance as indicated by the data shown from left to right beginning with column 1 through column 9 (excluding column T). The results for P4 and P5 show similar performance as indicated by the data shown from left to right beginning with column 1 through column 11 (excluding column T).

The following numbers identifying the products are ppm, which have been dosed.

TABLE 11

TREATMENT OF YEAST MILK IN THE PRESENCE OF PRODUCTS 4 AND 5

| | No acidic treatment | | Treatment H2SO4 pH 1.6 | | Treatment H2SO4 pH 1.8 | |
|---|---|---|---|---|---|---|
| | Viability % | Flocculation Rate | Viability % | Flocculation Rate | Viability % | Flocculation Rate |
| Conventional Treatment | 91.2 | 3.9 | 82.7 | 1.4 | 89.6 | 2.2 |
| Kamoran HJ - 5 ppm | 81.8 | 2.4 | — | — | 84.0 | 1.7 |
| Product 4 - 50 ppm | 91.2 | 4.7 | 87.2 | 1.3 | 88.0 | 1.76 |
| Product 4 - 70 ppm | 90.0 | 2.8 | 92.5 | 1.62 | 91.2 | 1.8 |
| Product 5 - 50 ppm | 89.6 | 3.2 | 88.5 | 1.78 | 87.4 | 2.0 |
| Product 5 - 70 ppm | 89.1 | 3.7 | 91.0 | 1.66 | 86.5 | 2.0 |

TABLE 12

ALCOHOLIC FERMENTATION TEST - FERMENTATION TUB

| Parameters | % Yeast Viability | % Yeast growth | Flocculation Rate | % Infection in Wine |
|---|---|---|---|---|
| Initial testimony | 85.6 | 11.3 | 6.95 | 10.3 |
| Final testimony | 89.8 | 8.1 | 6.16 | 9.5 |
| Kamoran HJ - 5 ppm | 83.3 | 11.7 | 2.10 | 8.0 |
| Product 4 - 50 ppm | 87.7 | 9.6 | 2.50 | 10.0 |
| Product 4 - 80 ppm | 86.3 | 13.6 | 2.40 | 15.8 |
| Product 5 - 50 ppm | 88.6 | 15.2 | 2.70 | 11.7 |
| Product 5 - 80 ppm | 84.6 | 9.7 | — | 9.3 |

Conclusion: In the treatment of yeast milk ("pé-de-cuba"), the mixtures 4 and 5 can be used from 50 ppm and associated to the conventional use of the sulfuric acid.

Therefore, the compositions of the present invention are useful:

As antimicrobial agents to prevent and treat diseases caused by fungi, protozoans or bacteria.

As a performance improver and anticoccidial in animal production.

To preserve food both for animals and human beings.

To conserve seeds.

To control bacterial infections in fermentations made by yeasts.

The invention claimed is:

1. A topical or oral antimicrobial composition consisting essentially of about 5-76% castor oil of the total weight of the composition and about 24-95% of cashew nut peel liquid of the total weight of the composition.

* * * * *